United States Patent [19]

Sim et al.

[11] Patent Number: 4,552,884
[45] Date of Patent: Nov. 12, 1985

[54] METHOD OF TREATING HEART DISEASE

[75] Inventors: Malcolm F. Sim, Woodborough; David B. Yates, Farnsfield, both of England

[73] Assignee: The Boots Company PLC, Nottingham, England

[21] Appl. No.: 689,180

[22] Filed: Jan. 7, 1985

[30] Foreign Application Priority Data

Jan. 13, 1984 [GB] United Kingdom ................ 8400905
Jan. 13, 1984 [GB] United Kingdom ................ 8400906

[51] Int. Cl.$^4$ ............................................. A61K 31/47
[52] U.S. Cl. ................................................. 514/312
[58] Field of Search ...................................... 514/312

[56] References Cited

U.S. PATENT DOCUMENTS 4,302,460 11/1981 Davies et al. ...................... 514/312
4,442,109 4/1984 Davies ............................... 514/312
4,447,435 5/1984 Davies ............................... 514/312

Primary Examiner—Douglas W. Robinson
Attorney, Agent, or Firm—Gordon W. Hueschen

[57] ABSTRACT

A method for the treatment of heart failure in a mammal comprises the administration to the mammal of a quinolone of the general formula I.

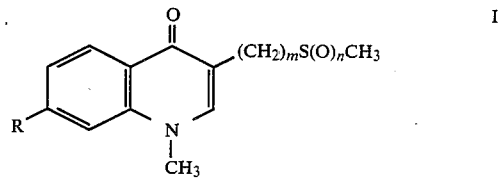

wherein m is 0 or 1; n is 0, 1 or 2; and R is hydrogen, halo, methyl or trifluoromethyl. A preferred method of the invention comprises the treatment of chronic heart failure in a mammal by the oral administration of a quinolone of formula I. Preferred compounds of formula I are 7-fluoro-1-methyl-3-methylsulphinyl-4-quinolone and 1-methyl-3-methylsulphonylmethyl-4-quinolone.

9 Claims, No Drawings

METHOD OF TREATING HEART DISEASE

This invention relates to a method for the treatment of heart failure.

In our British Patent Specification Nos. 2,047,691B and 2,085,411B there are described quinolone derivatives with antihypertensive activity and methods for their preparation. We have now found that certain of these quinolone derivatives are useful for the treatment of heart failure.

The present invention provides a method for the treatment of heart failure in a mammal which comprises the administration to the mammal of a quinolone of the formula I

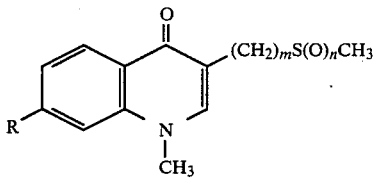

wherein m is 0 or 1; n is 0, 1 or 2; and R is hydrogen halo, methyl or trifluoromethyl.

The term "halo" denotes fluoro, chloro or bromo.

Heart failure is an important disease in which the heart fails to maintain an adequate circulation for the needs of the body, causing disability or death. The symptoms of heart disease include dyspnoea, fatigue, peripheral oedema and congestion of visceral organs.

Many cases of heart failure have an ischaemic aetiology but other causes, are, for example, valvular heart disease and primary or secondary cardiomyopathies.

We have now found that, in standard laboratory mammals, for example dogs, the compounds of formula I are vasodilators with a dilating action on both arteriolar and venous vascular beds. Accordingly the compounds are useful for the treatment of heart failure in mammals.

The method of the present invention may be used acutely, for example in the treatment of heart failure complicating acute myocardial infarction. However a preferred method of the present invention is the treatment of chronic heart failure, for example, chronic congestive heart failure.

Since the compounds of formula I have a dilating effect on both arteriolar and venous vascular beds, they not only decrease systemic vascular resistance and increase cardiac output, but also decrease systemic and pulmonary venous pressures. This is an important advantage in the treatment of heart failure, especially chronic heart failure.

It has also been found that the compounds of formula I have positive inotropic activity, which is an additional advantage in the treatment of heart failure.

As used hereinafter, the term "active compound" denotes a quinolone of general formula I.

In the method of the present invention, the active compound may be administered enterally or parenterally. Enteral administration may be oral or rectal. Parenteral administration may be intravenous, or topical. Oral administration is preferred for the treatment of chronic heart failure, but intravenous administration may be preferred in treating the acute stage of this disease, for example, heart failure complicating acute myocardial infarction.

In the method of the present invention, the active compound is generally administered in the form of a pharmaceutical composition comprising the active compound together with a pharmaceutically acceptable carrier. Such pharmaceutical compositions may take the form of any of the known pharmaceutical compositions for enteral or parenteral administration. Pharmaceutically acceptable carriers suitable for use in such compositions are well known in the art of pharmacy. The compositions of the invention suitably contain 0.1–90% by weight of active compound. The compositions of the invention are often prepared in unit dosage form.

Compositions for oral administration are the known pharmaceutical forms for such administration, for example tablets, capsules, syrups and aqueous or oily suspensions. The excipients used in the preparation of these compounds are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly capsules, for example hard or soft gelatin capsules, containing the active compound with or without added excipients, may be prepared by conventional means and, if desired, provided with enteric coatings in a known manner. The tablets and capsules may conveniently each contain 5–200 mg. of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example, sterile suspensions in aqueous and oily media or sterile solutions in a suitable solvent.

Compositions for topical administration may comprise a matrix in which the active compound is dispersed so that the compound can be held in contact with the skin in order to administer the active compound transdermally. Alternatively the active compound may be dispersed in a cream or ointment base.

In some formulations it may be beneficial to use the compounds of the present invention in the form of particles of very small size, for example, as obtained by fluid energy milling.

In the compositions of the present invention the active compound may, if desired, be associated with other compatible pharmacologically active ingredients, for example, a diuretic, such as frusemide or bendrofluazide.

For enteral administration, a suitable dose for administration to mammals, including man, is generally within the range 0.015–15 mg/kg/day, more usually 0.3–7.0 mg/kg/day, and especially 0.5–5.0 mg/kg/day, given in single or divided doses. For parenteral administration, a suitable dose is generally within the range 0.0015–1.5 mg/kg/day, more usually 0.03–0.7 mg/kg/day given in single or divided doses.

The compounds of formula I wherein m is 1, for example, 1-methyl-3-methylsulphonylmethyl-4-quinolone, form acid addition salts with strong acids, for example hydrochloric acid. It will be appreciated that such salts, provided that they are therapeutically acceptable, may be used therapeutically in place of the bases of formula I wherein m is 1.

Valuable compounds for use in the method of the present invention are 7-fluoro-1-methyl-3-methylthio-4-quinolone, 7-chloro-1-methyl-3-methylthio-4-quinolone and 7-chloro-1-methyl-3-methylthiomethyl-4-quinolone.

Particularly valuable compounds for use in the method of the present invention are those of the formula II,

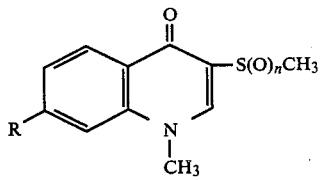

wherein n is 1 or 2, preferably 1, and R is hydrogen, halo, methyl or trifluoromethyl.

Specific quinolones within general formula II are the following compounds.
1-methyl-3-methylsulphinyl-4-quinolone
7-chloro-1-methyl-3-methylsulphinyl-4-quinolone
7-fluoro-1-methyl-3-methylsulphinyl-4-quinolone
7-bromo-1-methyl-3-methylsulphinyl-4-quinolone
1,7-dimethyl-3-methylsulphinyl-4-quinolone
1-methyl-3-methylsulphinyl-7-trifluoromethyl-4-quinolone
7-fluoro-1-methyl-3-methylsulphonyl-4-quinolone Other particularly valuable compounds for use in the method of the present invention are those of the formula III,

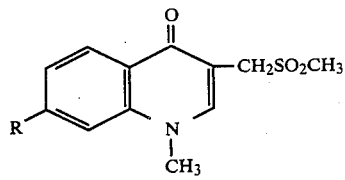

wherein R is hydrogen, fluoro, chloro, methyl or trifluoromethyl.

Specific quinolones within formula III are the following compounds.
1-methyl-3-methylsulphonylmethyl-4-quinolone
7-chloro-1-methyl-3-methylsulphonylmethyl-4-quinolone
7-fluoro-1-methyl-3-methylsulphonylmethyl-4-quinolone
1-methyl-3-methylsulphonylmethyl-7-trifluoromethyl-4-quinolone
1,7-dimethyl-3-methylsulphonylmethyl-4-quinolone.

Especially valuable compounds for use in the method of the present invention are those of formulae II and III wherein R is hydrogen or fluoro. The preferred compounds are 7-fluoro-1-methyl-3-methylsulphinyl-4-quinolone and 1-methyl-3-methylsulphonylmethyl-4-quinolone.

The haemodynamic effects of 7-fluoro-1-methyl-3-methylsulphinyl-4-quinolone and 1-methyl-3-methylsulphonylmethyl-4-quinolone were studied in anaesthetised dogs at dosages between 1 and 10 mg/kg given intravenously. The haemodynamic effects showed that the compounds are vasodilators, with a dilating action on both arteriolar and venous vascular beds.

The inotropic activities of 7-fluoro-1-methyl-3-methylsulphinyl-4-quinolone and 1-methyl-3-methylsulphonylmethyl-4-quinolone were determined by a method similar to that described by Markis, J. E. and Koch-Weser, J. in Journal of Pharmacology and Experimental Therapeutics, 1971, Vol. 78 No. 1. pp. 94–101. Intact left atria from guinea pigs were used in the determinations, and the animals were treated with reserpine, 5 mg/kg given intraperitoneally, 24 hours before removal of the atria. It was found that both compounds have positive inotropic activity.

The following are examples of compositions which may be used in accordance with the method of the present invention.

Composition 1

In the preparation of capsules, 100 parts by weight of active compound and 250 parts by weight of lactose are de-aggregated and blended. The mixture is filled into hard gelatin capsules, each capsule containing 100 mg of active compound.

Composition 2

In the preparation of capsules, 50 parts by weight of active compound and 300 parts by weight of lactose are de-aggregated and blended. The mixture is filled into hard gelatin capsules, each capsule containing 50 mg of active compound.

Composition 3

Tablets are prepared from the following ingredients.

|  | parts by weight |
| --- | --- |
| Active compound | 100 |
| Lactose | 100 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tableting machine to give tablets containing 100 mg active compound.

Composition 4

Capsules are prepared as described in Example 2 in which the active ingredient is 7-fluoro-1-methyl-3-methylsulphinyl-4-quinolone or 1-methyl-3-methylsulphonylmethyl-4-quinolone.

Composition 5

Tablets are prepared as described in Example 3 in which the active ingredient is 7-fluoro-1-methyl-3- methylsulphinyl-4-quinolone or 1-methyl-3-methylsulphonylmethyl-4-quinolone.

Composition 6

In the preparation of capsules, 100 parts by weight of micronised 7-fluoro-1-methyl-3-methylsulphinyl-4-quinolone and 178 parts by weight of lactose are de-aggregated and blended. The mixture is filled into hard gelatin capsules, each capsule containing 100 mg of 7-fluoro-1-methyl-3-methylsulphinyl-4-quinolone.

The following non-limitative Example illustrates the invention.

EXAMPLE

In a clinical study, eleven patients presented with chronic congestive heart failure which was not controlled by a daily oral dosage of 120 mg frusemide (more in some patients) together with 10 mg amiloride. This diuretic therapy was continued together with a single oral dosage of 7-fluoro-1-methyl-3-methylsulphinyl-4-quinolone, given in capsules prepared as described in Composition 6 above. Patients A and B received 200 mg (2 capsules) and the remainder received 100 mg (1 capsule) of the quinolone.

Cardiac output and pulmonary capillary wedge pressure were monitored in the patients before treatment with the quinolone, during 8 hours after treatment and again at 24 hours after treatment with the quinolone. Cardiac output was measured by a thermodilution method and pulmonary capillary wedge pressure was measured by means of a Swan-Ganz balloon catheter with the tip of the catheter "wedged" in a branch of the pulmonary artery.

Patient A did not complete the trial due to a technical failure in the use of the equipment. Patient B was withdrawn from the trial due to ventricular tachycardia. A further patient was withdrawn from the trial due to apparent non-compliance with the dosage regimen.

In the remaining 8 patients who completed the trial, a statistically significant and clinically significant increase in cardiac output and reduction in pulmonary capillary wedge pressure were observed during the initial 8-hour period following treatment and this clinical improvement was still present 24 hours after treatment.

We claim:

1. A method for the treatment of heart failure in a mammal which comprises the administration to a mammal with heart failure of a therapeutically effective amount of a quinolone of the formula I,

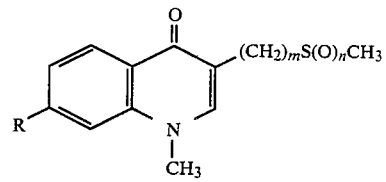

wherein m is 0 or 1, n is 0, 1 or 2; and R is hydrogen, halo, methyl or trifluoromethyl.

2. A method as claimed in claim 1 wherein the quinolone is administered orally to a mammal with chronic heart failure.

3. A method as claimed in claim 2 wherein the quinolone has the formula II,

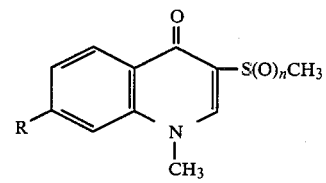

wherein n is 1 or 2 and R is hydrogen, halo, methyl or trifluoromethyl.

4. A method as claimed in claim 3 wherein n is 1.

5. A method as claimed in claim 3 wherein R is fluoro.

6. A method as claimed in claim 5 wherein the quinolone is 7-fluoro-1-methyl-3-methylsulphinyl-4-quinolone.

7. A method as claimed in claim 6 wherein the mammal is a human.

8. A method as claimed in claim 2 wherein the quinolone has the formula III,

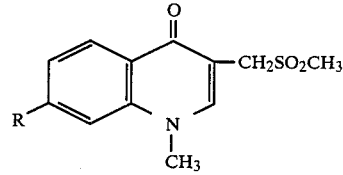

wherein R is hydrogen, fluoro, chloro, methyl or trifluoromethyl.

9. A method as claimed in claim 8 wherein the quinolone is 1-methyl-3-methylsulphonylmethyl-4-quinolone.

* * * * *

UNITED STATES PATENT AND TRADEMARK OFFICE

CERTIFICATE EXTENDING PATENT TERM
UNDER 35 U.S.C. § 156

PATENT NO.: 4,552,884

DATED: November 12, 1985

INVENTORS: Malcolm F. Sim et al.

PATENT OWNER: The Boots Company PLC

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,509 DAYS with all rights pertaining thereto as provided by 35 U.S.C. § 156(b).

I have caused the seal of the Patent and Trademark Office to be affixed this 20th day of September 1994.

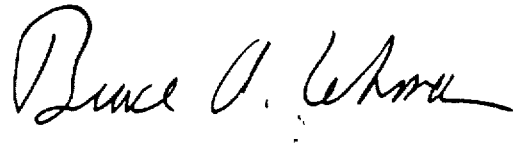

Bruce A. Lehman
Assistant Secretary of Commerce and
Commissioner of Patents and Trademarks